United States Patent [19]

Kawata et al.

[11] 4,343,789

[45] Aug. 10, 1982

[54] SUSTAINED RELEASE PHARMACEUTICAL COMPOSITION OF SOLID MEDICAL MATERIAL

[75] Inventors: Hiroitsu Kawata, Kawagoe; Masayoshi Aruga, Ageo; Tadayoshi Ohmura, Niiza; Takashi Sonobe, Saitama; Satoru Yoneya, Omiya; Chiharu Sone, Matsudo, all of Japan

[73] Assignee: Yamanouchi Pharmaceutical Co., Ltd., Tokyo, Japan

[21] Appl. No.: 165,244

[22] Filed: Jul. 2, 1980

[30] Foreign Application Priority Data

Jul. 5, 1979 [JP] Japan .................................. 54/85209
Mar. 22, 1980 [JP] Japan ................................. 55/36514

[51] Int. Cl.$^3$ .......................... A61K 9/14; A61K 9/16; A61K 9/20; A61K 31/74
[52] U.S. Cl. ....................................... 424/78; 424/19; 424/22; 424/31; 424/32; 424/33; 424/35; 424/80; 424/81
[58] Field of Search ...................... 424/19–22, 424/35, 78, 80, 362; 264/117, 118

[56] References Cited

U.S. PATENT DOCUMENTS

| | | | |
|---|---|---|---|
| 2,149,005 | 2/1939 | Bockmuhl et al. | 424/14 |
| 2,540,253 | 2/1951 | Gakenheimer | 424/78 |
| 2,698,822 | 1/1955 | Halpern et al. | 424/271 |
| 3,297,804 | 1/1967 | Iwamoto et al. | 264/118 |
| 3,308,217 | 3/1967 | Lowy et al. | 264/117 |
| 3,325,362 | 6/1967 | Poole | 424/285 |
| 3,374,146 | 3/1968 | Blicharz et al. | 424/19 |
| 3,458,622 | 7/1969 | Hill | 424/22 |
| 3,634,584 | 1/1972 | Poole | 424/22 |
| 3,670,065 | 6/1972 | Eriksson et al. | 424/19 |
| 3,692,896 | 9/1972 | Tsumura et al. | 424/78 |
| 3,852,421 | 12/1974 | Koyanagi et al. | 424/362 |
| 3,862,311 | 1/1975 | Leeson | 424/78 |
| 4,017,598 | 4/1977 | Ohno et al. | 424/362 |
| 4,017,647 | 4/1977 | Ohno et al. | 424/35 |
| 4,086,346 | 4/1978 | Bocker et al. | 264/117 |
| 4,127,647 | 11/1978 | Sato et al. | 424/78 |
| 4,132,753 | 1/1979 | Blicharz et al. | 264/117 |
| 4,151,273 | 4/1979 | Riegelman et al. | 424/78 |
| 4,159,345 | 6/1979 | Takeo et al. | 424/362 |
| 4,180,559 | 12/1979 | Huber | 424/35 |
| 4,252,786 | 2/1981 | Weiss et al. | 424/35 |
| 4,254,099 | 3/1981 | Asmussen et al. | 424/80 |
| 4,269,859 | 5/1981 | Morse | 424/362 |

FOREIGN PATENT DOCUMENTS

| | | |
|---|---|---|
| 2400819 | 7/1975 | Fed. Rep. of Germany . |
| 2822882 | 12/1978 | Fed. Rep. of Germany . |
| 2847237 | 5/1980 | Fed. Rep. of Germany . |
| 54-44034 | 4/1979 | Japan . |
| 54-46837 | 4/1979 | Japan . |
| 55-22631 | 2/1980 | Japan . |
| 55-47615 | 4/1980 | Japan . |
| 55-64570 | 5/1980 | Japan . |

OTHER PUBLICATIONS

Chem. Abstracts 91 #96630h (1979) of Kanebo, Ltd., Jpn. Kokai Tokkyo Koho 79 44,034, Apr. 7, 1979, Coronary vasodilating compositions containing nifedipine.
Chem. Abstracts 93 #155846z, (1980) of Ohta Pharm., Jpn. Kokai Tokkyo Koho 80 22,631, Feb. 18, 1980, Nifedipine pharmaceuticals for easier absorption.
Chem. Abstracts 93 #210260f (1980) of Taiyo Yakuhin, Jpn. Kokai Tokkyo Koho 80 47,615, Apr. 4, 1980, Stable solid pharmaceuticals of nifedipine.
Chem. Abstracts 93 #220596j (1980) of Bayer A/G, Jpn. Kokai Tokkyo Koho 80 64,570, May 15, 1980.
Chem. Abstracts 93 #150124c (1980) of Bayer A/G, Ger. Offen. 2,847,237, May 14, 1980.
Chem. Abstracts 83 #209407w (1975) of Ger. Offen. 2,400,819 Jul. 17, 1975, Finely divided preparation of difficultly soluble pharmaceuticals, Kramer R. R. Amor et al.
Chem. Abstracts 87 #28914w (1977) of Eckert, T. et al. Arch. Pharm. (Weinhelm, Ger.) 1977, 310(2), 116–118, Polymorphic modifications of Nifedipine from supercooled melts.
Chem. Abstracts 90 #109987m (1979) of Ger. Offen. 2,822,882 Dec. 21, 1978, Kawata et al., Nifedipine solid preparations.
Chem. Abstracts 91 #112451h (1979) of Jpn. Kokai Tokkyo Koho 79 46,837, Apr. 13, 1979 Kanebo, Ltd., Nifedipine-containing vasodilating compositions with good absorption.

*Primary Examiner*—Shep K. Rose
*Attorney, Agent, or Firm*—Burgess, Ryan and Wayne

[57] ABSTRACT

Sustained release pharmaceutical composition of a solid medical material which contains an amorphous solid medical material, polyethylene oxide, and at least one basic substance selected from the group consisting of hydroxypropylmethyl cellulose, hydroxypropyl cellulose, methyl cellulose, polyvinyl pyrrolidone, carboxyvinyl polymer, hydroxypropylmethyl cellulose phthalate, cellulose acetate phthalate, methyl metaacrylate meta-acrylic acid copolymer, polyvinylacetal diethylaminoacetate, dimethylaminoethyl meta-acrylate meta-acrylic acid copolymer, 2-methyl-5-vinylpyridinemethyl acrylate meta-acrylic acid copolymer, citric acid, urea, succinic acid and amino acid, and may further contain one basic substance selected from the group consisting of a surface active agent, polyethylene glycol, propylene glycol, glycerin, a glycerin fatty acid ester and a vegetable oil (first embodiment): and in the case where the solid medical material is nicardipine, the composition may consist only of the amorphous nicardipine or a salt thereof without the above compound (second embodiment).

13 Claims, No Drawings

SUSTAINED RELEASE PHARMACEUTICAL COMPOSITION OF SOLID MEDICAL MATERIAL

DETAILED EXPLANATION OF THE INVENTION

The present invention relates to a sustained release pharmaceutical composition of a solid medical material.

A sustained release pharmaceutical composition has many advantages from a medical viewpoint such as the reduction of administration times, the decrease of side effects and the retention of effective concentration of medical material in blood. Therefore, various sustained release pharmaceutical compositions have hitherto been developed, for example, a pharmaceutical composition containing great amount of excipient which is difficult to be disintegrated in the stomach or intestines, a pharmaceutical composition in the form of a granule or tablet coated with a repellent, a pharmaceutical composition filmed with a semipermeable membrane, a pharmaceutical composition in which a polymer having low solubility or being hydrophilic is mixed with, adsorbed in or combined with a medical material to gradually release medical material. As the polymer used for this purpose, there are acid-type carboxyvinyl polymers, polyvinyl alcohol, polyacrylic acid, etc. However, a sustained release pharmaceutical composition usually can not avoid lowering the bioavailability accompanied with the sustaining release effect. Particularly, where a medical material itself has low solubility, sometimes the constant effective concentration of a medical material in blood can not be obtained. Accordingly, for such medical material, it has been greatly desired to obtain a pharmaceutical composition which possesses high solubility and superior sustained release activity.

Under these circumstances, the inventors of the present invention have found that a pharmaceutical composition having high solubility and superior sustained release activity can be obtained by utilizing a medical material in amorphous form.

That is, the object of the present invention is to provide a pharmaceutical composition having high solubility and superior sustained release activity by compounding a medical material, polyethylene oxide, and at least one basic substance (1st component) selected from the group consisting of hydroxypropylmethyl cellulose, hydroxypropyl cellulose, methyl cellulose, polyvinyl pyrrolidone, carboxyvinyl polymer, hydroxypropylmethyl cellulose phthalate, cellulose acetate phthalate, methyl meta-acrylate meta-acrylic acid copolymer, polyvinylacetal diethylaminoacetate, dimethylaminoethyl meta-acrylate meta-acrylic acid copolymer, 2-methyl-5-vinylpyridinemethyl acrylate meta-acrylic acid copolymer, citric acid, urea, succinic acid and amino acid. This pharmaceutical composition may further contain at least one basic substance (2nd component) selected from the group consisting of a surface active agent, polyethylene glycol, propylene glycol, glycerin, a glycerin fatty acid ester and vegetable oil.

As the result of a further investigation of the pharmaceutical composition containing nicardipine (chemical name: 2,6-dimethyl-4-(3'-nitrophenyl)-1,4-dihydropyridin-3,5-dicarboxylic acid-3-methyl ester 5-$\beta$-(N-benzyl-N-methylamino)-ethyl ester) among the above solid medical materials, the inventors of the present invention have found that a sustained release pharmaceutical composition of nicardipine can be obtained by using amorphous nicardipine or a salt thereof without the addition of any other substances possessing sustained release activity.

Accordingly, another object of the present invention is to provide a sustained release pharmaceutical composition of nicardipine which contains amorphous nicardipine or a salt thereof. This pharmaceutical composition need not contain the above 1st component as well as a 2nd component to possess the sustained release activity, but if desired, it can contain such substances.

The sustained release pharmaceutical composition of a solid medical material of the first object of the present invention can be obtained by the following method.

A solid medical material and the above basic substance(s), that is, the 1st component(s) or the 1st component(s) and the 2nd component(s), are dissolved in an organic solvent such as methanol, ethanol, chloroform, dichloromethane, singly or in a combination thereof, or water, and then the solvent is removed. The removal of the solvent is carried out by drying under reduced or normal pressure, spray drying, fluidized-bed granulating drying, or lyophilization, etc. By the above procedures, the fine powder or fine particle granules are obtained in which a solid medical material is dissolved or dispersed uniformly in amorphous form in the basic substance(s). Then, polyethylene oxide is added to the fine powder or fine particle granules thus obtained followed by mixing them to provide the sustained release pharmaceutical composition of the present invention.

This pharmaceutical composition also can be obtained by adding polyethylene oxide and the basic substance(s), that is, the 1st component(s) or the 1st component(s) and 2nd component(s) simultaneously, wherein polyethylene oxide is uniformly dissolved or dispersed with a solid medical material in the basic substance(s). Instead of polyethylene oxide, carboxypolymethylene (carbopol) can be also used as an equivalent material.

As the solid medical material in the present invention, any medical material having low or high solubility can be used if desired, to be maintained in the gastro-enteric tracts for long time. And the examples thereof are nicardipine hydrochloride, nifedipine, indenerol, indomethacin, buformin hydrochloride, etc.

As the amino acid of the 1st component, there are threonine, glycine, alanine, cysteine, lysine, etc. As the surface active agent of 2nd substance, there are anionic surface active agents such as sodium alkylsulfate, nonionic surface active agents such as polyoxyethylene sorbitan fatty acid ester, polyoxyethylene fatty acid ester, polyoxyethylene castor oil derivative, etc. And as the vegetable oil, there are sesame oil, corn oil, soybean oil, rapeseed oil, olive oil, coconut oil, etc.

The compounding ratio of each component in the pharmaceutical composition may vary according to the kind of a solid medical material or its administration dose. Usually, it is proper to use 0.5–20 parts by weight, preferably 1–10 parts by weight of the 1st component(s), 0.05–10 parts by weight, preferably 0.1–5 parts by weight of the 2nd component(s), per one part by weight of the solid medical material. The compounding ratio of polyethylene oxide is properly 0.1–50 parts by weight, preferably 0.5–30 parts by weight, per one part by weight of total amount of the solid medical material, the 1st component(s) and the 2nd component(s).

The sustained release pharmaceutical composition thus obtained is characterized in that polyethylene oxide is compounded in the form of a fine powder or fine particle granules in which the solid medical material is present in amorphous form. Hitherto, polyethylene oxide has been used as a coating agent or a binder in the preparation of pharmaceutical compositions, but it has not been reported that a sustained release pharmaceutical composition can be obtained by compounding polyethylene oxide with a solid medical material in amorphous form as described in the present invention. And the sustained release pharmaceutical composition of the present invention can provide not only the sustained release effect but the good adsorbability of a medical material, so that it gives high bioavailability.

The pharmaceutical compositions of the present invention can be practically used in formulations such as powders, granules, tablets, pills, capsules, by a conventional manner. In the preparation of such formulations, there may be used a conventional diluting agent, binder, a viscosity-increasing agent, etc. Further, according to the kind of a solid medical material, a compound for dissolving quickly the medical material can be added in the pharmaceutical composition or the treatment for dissolving the composition in the intestines can be applied.

As mentioned above, the other object of the present invention is to provide a sustained release pharmaceutical composition of nicardipine which possesses a coronary and cerebral vascular dilator activity and is useful for curing cerebral vascular disease, hypertention and angina pectoris. Hitherto, it has been difficult to provide a sustained release pharmaceutical composition of nicardipine because of its low solubility in the intestines. That is, nicardipine or a salt thereof can be easily dissolved in the first liquid (artificial gastric juice) of Japanese Pharmacopeia, so that it provides sufficiently the medical activity by usual formulations, but is slightly dissolved in the second liquid (artificial intestinal juice).

Under these circumstances, the inventors of the present invention have found that a sustained release pharmaceutical composition of nicardipine can be obtained by using amorphous nicardipine without adding any substance improving the solubility in the intestines. This composition can constantly sustain the effective concentration of nicardipine in blood for a long period of time because of its superior absorbability in the intestinal tract membrane in spite of low solubility of nicardipine in the intestinal juice.

Amorphous nicardipine used in the present invention can be prepared by friction-pulverizing the powder of nicardipine, preferably, by pulverizing the powder of nicardipine to a fine powder using a ball mill or a vibrating ball mill.

In the pulverizing step, it is desired to add some substances to decrease the adherence and massing of nicardipine so that nicardipine can be completely pulverized to fine powder. Examples of such substances are calcium lactate, TC-5 (trade name, Shinetsu Kagaku Kogyo Co., ingredient: hydroxypropylmethyl cellulose), Avicel (trade name, Asahikasei Kogyo Co., ingredient: crystalline cellulose), etc. The change of nicardipine or its salt to the amorphous form in the pulverizing step can be confirmed by X-ray diffraction.

The compound ratio of the powder of nicardipine can be properly controlled, and is usually 5–90%, preferably 10–70%, more preferably 20–40% of the total weight of the composition. The powder of nicardipine is usually in the crystalline form, for example, nicardipine hydrochloride is a crystal having a melting point of 168°–170° C. But, it can be possible to produce amorphous nicardipine in the synthesis step or purification step of nicardipine, and in that case the formed amorphous nicardipine can be used as it is for preparing the composition of the present invention.

The fine powder of amorphous nicardipine in the present invention can give the sustained release effect only by applying some coating to avoid the disintegration and dissolution in stomach. And further, it can give such an effect by adding a pH-depending agent, a viscosity-increasing agent or a water-insoluble agent before or after the pulverizing step.

As the pH-depending agent, there are the bases soluble in the intestines such as cellulose acetate phthalate, hydroxypropylmethyl cellulose, Eudragit L, S, RL and RS (trade names, Rohm and Haas Co., ingredient: acrylic acid meta-acrylic acid ester copolymer, or meta-acrylic acid meta-acrylic acid ester copolymer), etc. As the viscosity-increasing agent, there are polyethylene oxide, Carbopol (trade name, B. F. Goodrich Co., ingredient: carboxyvinyl polymer), sodium polyacrylate, sodium arginate, carboxymethyl cellulose calcium, carboxymethyl cellulose sodium, polyethylene glycol (molecular weight: 6000–20000), etc. And as the water-insoluble agent, there are crystalline cellulose (for example, Avicel (trade name)), calcium phosphate, etc.

Polyethylene oxide is a homo polymer of the formula $+O-CH_2-CH_2+_n$ wherein n is from about 2,000 to about 100,000. Thus, molecular weights range from about 100,000 to about 5,000,000. These polymers are in solid form. Polyethylene oxide resins are readily available and are sold as Polyox resins by Union Carbide Corporation. Polyethylene glycols such as, for example, the Carbowax products sold by Union Carbide Corporation, is a polymer of the formula $HOCH_2(CH_2OCH_2)_nCH_2OH$. Generally, the molecular weight range of the polyethylene glycols is from about 200 to about 14,000. Up to a molecular weight of about 600, the polyethylene glycols are in liquid form. From molecular weights of about 1,000 to about 1,450, they are in a soft solid form. At molecular weights of about 3,350 to about 14,000 they are in solid form.

The compound ratio of the above agents can be properly controlled according to the formulations practically used. The adsorption amount of nicardipine can be controlled by the pulverizing degree of nicardipine or addition amount of the above agents, so that it is possible to control the medical effect and effective time of nicardipine.

The pharmaceutical composition of the present invention are prepared in the form of granules, tablets, pills, capsules, etc., by a conventional manner. In the preparation of these formulations, there can be added a diluting agent, binder, ingrediating agent, etc., conventionally used.

Then, the present invention is explained in detail by the following Experiment and Examples.

EXPERIMENT

Control:

After pulverizing the crystalline powder of nicardipine hydrochloride by sample mill (using 1 mm screen), mini-tablets each weighing of 35 mg were prepared by a conventional manner according to the following formulation. The tablets were coated with cellulose acetate phthalate, the film of which is soluble in the intestines to provide tablets soluble in the intestines.

| Formulation | |
|---|---|
| Nicardipine hydrochloride | 5.0 mg |
| Lactose | 20.3 mg |
| Corn starch | 7.0 mg |
| Hydroxypropyl cellulose | 1.4 mg |
| Carboxymethyl cellulose calcium | 1.1 mg |
| Magnesium stearate | 0.2 mg |
| | 35.0 mg |

Pharmaceutical Composition of the present invention:

20 g of the crystalline powder of nicardipine hydrochloride, 4 g of TC-5 (trade name) and 38 g of Avicel (trade name) were pulverized for 16 hours by a vibrating ball mill, whereby the crystals of nicardipine hydrochloride changed to the amorphous form. Using the powder thus obtained, the tablets each weighing 312 mgs were prepared according to the following formulation, and they were then coated with cellulose acetate phthalate to be dissolved in the intestines.

| Formulation | |
|---|---|
| Nicardipine hydrochloride | 40 mg |
| TC-5 | 8 mg |
| Avicel | 76 mg |
| Particles 209 for direct compression (Fiji Kagaku Kogyo Co.) | 120 mg |
| Carboxymethyl cellulose calcium | 64 mg |
| Magnesium stearate | 4 mg |
| | 312 mg |

| | | Concentration in blood when orally administered to dogs: | | | | | | | | | |
|---|---|---|---|---|---|---|---|---|---|---|---|
| Sample | Number of dogs | Dose | Concentration in blood plasma (ng/Kg) | | | | | | | | Area under the curve of con. in blood plasma [(ng/Kg) . hr)] |
| | | | 1hr. | 2hr. | 3hr. | 4hr. | 6hr. | 8hr. | 10hr. | 12hr. | |
| Control | 6 | 5mg/Kg | 7.7 | 6.9 | 3.4 | 1.3 | 0.1 | 9.2 | — | — | 29.35 |
| Phrm. Com. of this invention | 6 | 10mg/Kg | 103.0 | 156.1 | 127.7 | 89.0 | 141.7 | 55.9 | 56.0 | 35.4 | 1062.90 |

EXAMPLE 1

1000 g of a mixture of dichloromethane and methanol (1:1 in weight ratio) was added to a mixture of 50 g of nicardipine hydrochloride and 100 g of hydroxypropylmethyl cellulose to provide a solution. The organic solvent of the solution was distilled off by spray-drying to provide a fine particle powder. To 50 g of the fine particle powder thus obtained were added 30 g of polyethylene oxide in the form of a fine particle powder and 3.3 g of talc, and they were mixed uniformly. Capsules were prepared by filling each 250 mg of the mixture in No. 1 capsules.

EXAMPLE 2

1000 g of dichloromethane was added to a mixture of 50 g of nifedipine, 50 g of polyethylene glycol 400 and 250 g of polyvinyl pyrrolidone to provide a solution, and 25 g of magnesium meta-silicate aluminate was dispersed uniformly in the solution. Using a fluidized-bed granulater, 350 g of anhydrous phosphoric acid hydrogen calcium was fluidized and sprayed with the above solution to provide fine granules. To 250 g of the fine granules thus obtained were added 89.5 g of polyethylene oxide in the form of a fine particle powder, 7 g of talc and 3.5 g of magnesium stearate, and they are mixed uniformly. Tablets each weighing 350 mg were prepared using an oblong punch having a major axis of 14 mm and a minor axis of 7 mm.

EXAMPLE 3

3000 g of a mixture of dichloromethane and methanol (1:1 in weight ratio) was added to a mixture of 100 g of indomethacin, 200 g of hydroxypropyl cellulose and 20 g of polyethylene oxide to provide a solution. The organic solvent of the solution was distilled off by spray-drying to provide a fine particle powder. To 160 g of the fine particle powder thus obtained were added 80 g of polyethylene oxide and 10 g of talc, and they were mixed uniformly. Capsules were prepared by filling each 250 mg of the mixture in No. 1 capsules.

EXAMPLE 4

400 g of methanol was added to a mixture of 20 g of nicardipine hydrochloride, 40 g of hydroxypropylmethyl cellulose phthalate and 10 g of polysorbate 80 to provide a solution. The organic solvent of the solution was distilled off by drying under reduced pressure to provide a solid material. The solid material was pulverized to fine particle powder. To 35 g of the fine particle powder thus obtained were added 105 g of fine crystalline cellulose, 80 g of polyethylene oxide and 10 g of talc, and they were mixed uniformly. Capsules were prepared by filling each 230 mg of the mixture in No. 1 capsules.

EXAMPLE 5

15 g of the crystalline powder of nicardipine hydrochloride, 3 g of TC-5 (trade name), 20.6 g of Avicel (trade name) and 18.2 g of HP-55 (trade name, Shinetsu Kagaku Kogyo Co., ingredient: hydroxypropylmethyl cellulose phthalate) were pulverized for 16 hours by a vibrating ball mill, whereby the crystals of nicardipine hydrochloride changed to the amorphous form. Using the powder thus obtained, the tablets each weighing 500 mg were prepared according to the following formulation.

| Formulation | |
|---|---|
| Nicardipine hydrochloride | 75 mg |
| TC-5 | 15 mg |
| Avicel | 103 mg |
| HP-55 | 91 mg |
| Particles 209 for direct compression | 125 mg |
| Carboxymethyl cellulose calcium | 20 mg |
| L-HPC (L-H31)* | 66 mg |
| Magnesium stearate | 5 mg |
| | 500 mg |

*L-HPC(L-H-31): trade name, Shinetsu Kagaku Kogyo Co. ingredient: lower substituted hydroxypropyl cellulose

EXAMPLE 6

20 g of the crystalline powder of nicardipine hydrochloride, 20 g of polyvinyl pyrrolidone K-30 (trade name, BASF Co.), HP-55 (trade name) and 4 g of Carbopol-940 (trade name) were pulverized for 16 hours by a vibrating ball mill, whereby the crystals of nicardipine hydrochloride changed to amorphous form. Using the powder thus obtained, tablets each weighing 360 mg were prepared according to the following formulation.

| Formulation | |
| --- | --- |
| Nicardipine hydrochloride | 60 mg |
| Polyvinyl pyrrolidone K-30 | 30 mg |
| HP-55 | 180 mg |
| Carbopol-940 | 12 mg |
| Polyethylene glycol 6000 | 48 mg |
| | 360 mg |

EXAMPLE 7

40 g of the crystalline powder of nicardipine hydrochloride, 200 g of calcium lactate and 20 g of polyethylene oxide 18 were pulverized for 10 hours by a vibrating ball mill, whereby the crystals of nicardipine hydrochloride changed to amorphous form. Using a fluidized-bed granulater ("Uniglat" trade name, Okawara Seisakusho Co.), 195 g of the powder thus obtained and 150 g of Kalica GS (trade name, Kyowa Kagaku Kogyo Co., ingredient: anhydrous phosphoric acid hydrogen calcium) were fluidized, sprayed with a solution of 20 g of polyethylene oxide-18 in 3000 ml of methylene chloride, and treated in a conventional manner to provide fine granules. Capsules were prepared by filling each 365 mg of the fine granules thus obtained in No. 1 capsules in a conventional manner.

EXAMPLE 8

40 g of nicardipine hydrochloride in the form of a crystalline powder, 80 g of Eudragit RL (trade name, Rohm and Haas Co., ingredient: acrylic acid meta-acrylic acid ester copolymer), 4 g of sodium arginate and 200 g of Avicel (trade name) were pulverized for 16 hours by a vibrating ball mill, whereby the crystals of nicardipine hydrochloride were changed to amorphous form. Using the powder thus obtained, tablets each weighing 600 mg were prepared according to the following formulation.

| Formulation | |
| --- | --- |
| Nicardipine hydrochloride | 60 mg |
| Eudragit RL | 120 mg |
| Sodium arginate | 6 mg |
| Avicel | 300 mg |
| Lactose | 78 mg |
| Corn starch | 30 mg |
| Magnesium stearate | 6 mg |
| | 600 mg |

EXAMPLE 9

50 g of a crystalline powder of nicardipine hydrochloride and 250 g of TC-5 (trade name) were pulverized for 16 hours by a vibrating ball mill, whereby the crystals of nicardipine hydrochloride changed to amorphous form. To 120 g of the powder thus obtained were added 140 g of lactose and 150 g of Avicel (trade name), and they were mixed uniformly. The mixed powder thus obtained was rotated in a coating pan used in a usual sugar coating, and sprayed with a solution of 10 g of methyl cellulose in 1000 g of water to provide pills of 32-18 mesh. Half of the amount of the pills thus obtained were recovered, and the remaining half of the pills was further rotated in the same coating pan and sprayed with a solution of 10 g of Eudragit RL (trade name) in a mixture of 70 g of acetone and 130 g of isopropanol. Then, whole pills were combined and mixed uniformly. Capsules were prepared by filling each 450 mg of the mixture in No. 0 capsules.

What is claimed is:

1. A sustained release pharmaceutical composition comprising a coronary and cerebral vascular dilating-effective amount of an amorphous form of nicardipine or a salt thereof, and polyethylene oxide in the form of a fine powder or fine particle granules.

2. A pharmaceutical composition as claimed in claim 1 which contains (i) said amorphous nicardipine or salt thereof, (ii) said polyethylene oxide and (iii) at least one basic substance (1st component) selected from the group consisting of hydroxypropylmethyl cellulose, hydroxypropyl cellulose, methyl cellulose, polyvinyl pyrrolidone, carboxyvinyl polymer, hydroxypropylmethyl cellulose phthalate, cellulose acetate phthalate, methyl meta-acrylate meta-acrylic acid copolymer, polyvinylacetal diethylaminoacetate, dimethylaminoethyl meta-acrylate meta-acrylic acid copolymer, 2-methyl-5-vinylpyridinmethyl acrylate meta-acrylic acid copolymer, citric acid, urea, succinic acid and an amino acid.

3. A pharmaceutical composition as claimed in claim 1 which contains (i) said amorphous nicardipine or salt thereof, (ii) said polyethylene oxide, (iii) said 1st component(s) and at least one basic substance (2nd component) selected from the group consisting of a surface active agent, polyethylene glycol, propylene glycol, glycerine, glycerine fatty acid ester and a vegetable oil.

4. The composition as claimed in claim 1 in which the amorphous nicardipine or its salt is obtained by friction pulverizing nicardipine or its salt to a fine powder.

5. The composition as claimed in claim 4 in which the friction pulverizing is performed by a ball mill or a vibrating ball mill.

6. A process of producing a sustained release pharmaceutical composition as claimed in claim 1 characterized by compounding said nicardipine or salt thereof in amorphous form with said polyethylene oxide.

7. The process of producing a sustained release pharmaceutical composition as claimed in claim 2 which comprises dissolving nicardipine or salt thereof in amorphous form and said 1st component(s) in water or an organic solvent, distilling off the solvent, and then adding said polyethylene oxide.

8. The process of producing a sustained release pharmaceutical composition as claimed in claim 3 which comprises dissolving said nicardipine or salt thereof in amorphous form, said 1st component(s) and said 2nd component(s) in water or an organic solvent, distilling off the solvent, and then adding said polyethylene oxide.

9. The process of producing a sustained release pharmaceutical composition as claimed in claim 2 which comprises dissolving said nicardipine or salt thereof in amorphous form, said 1st component(s) and said polyethylene oxide in water or an organic solvent, and then distilling off the solvent.

10. The process of producing a sustained release pharmaceutical composition as claimed in claim 3 which comprises dissolving said nicardipine or salt thereof in amorphous form, said 1st component(s), said 2nd component(s) and said polyethylene oxide in water or an organic solvent, and distilling off the solvent.

11. The composition as claimed in claim 1, wherein said nicardipine is in the form of amorphous nicardipine base.

12. The composition as claimed in claim 1, wherein said amorphous salt of nicardipine is amorphous nicardipine hydrochloride.

13. The process as claimed in claim 6, in which said amorphous nicardipine or salt thereof is obtained by friction pulverizing nicardipine or a salt thereof to a fine powder.

* * * * *